United States Patent [19]

Krivoshlykov et al.

[11] Patent Number: 5,370,643
[45] Date of Patent: Dec. 6, 1994

[54] MULTIPLE EFFECT LASER DELIVERY DEVICE AND SYSTEM FOR MEDICAL PROCEDURES

[75] Inventors: Sergei G. Krivoshlykov, Moscow, Russian Federation; Wolfgang Neuberger, Monchengladbach, Germany

[73] Assignee: CeramOptec, Inc., Enfield, Conn.

[21] Appl. No.: 161,327

[22] Filed: Dec. 2, 1993

Related U.S. Application Data

[63] Continuation-in-part of Ser. No. 908,379, Jul. 6, 1992.

[51] Int. Cl.$^5$ .......................... A61B 17/36; G02B 6/18
[52] U.S. Cl. .......................................... 606/16; 606/2;
606/15; 385/124; 385/117
[58] Field of Search ........................ 606/2, 3, 13, 1, 17;
607/89; 385/116, 117, 124

[56] References Cited

U.S. PATENT DOCUMENTS

| | | |
|---|---|---|
| 4,421,382 | 12/1983 | Doi et al. . |
| 4,576,160 | 3/1986 | Tanaka . |
| 4,593,975 | 6/1986 | Nakauchi et al. ................. 385/124 |
| 4,674,843 | 6/1987 | Baba et al. ...................... 385/124 |
| 4,693,244 | 9/1987 | Daikuzono . |
| 4,963,143 | 10/1990 | Pinnow ............................ 606/17 |
| 4,973,330 | 11/1990 | Azema et al. . |
| 5,005,180 | 4/1991 | Edelman et al. ................... 606/10 |
| 5,050,597 | 9/1991 | Daikuzono . |
| 5,057,099 | 10/1991 | Rink . |
| 5,102,410 | 4/1992 | Dressel . |

Primary Examiner—Stephen C. Pellegrino
Assistant Examiner—Michael Peffley
Attorney, Agent, or Firm—Kenneth P. Glynn; Diane L. Ferrone; Stephen J. Driscoll

[57] ABSTRACT

It is the object of this invention to provide a new and highly flexible medical laser delivery device and system with the abilty to change the radiation pattern delivered without the need to change or modify the output end or output optics. The output optics or output end is frequently embodied in the body and/or is sterile and its change or modification or the change of the whole delivery device during the procedure is undesirable. Changing the input pattern while using conventional step index fibers cannot achieve the required result of control of the output pattern in a reliable manner because of beam spreading over the length of the device. The light becomes diffused over the length of the conventional step index fiber. It is therefore another object of the present invention to specify the requirements for the transmission fiber employed in the device and a method of making same. Still another object of the invention is to achieve effective feedback control for the laser delivery device to control such important parameters as power output and output pattern.

19 Claims, 4 Drawing Sheets

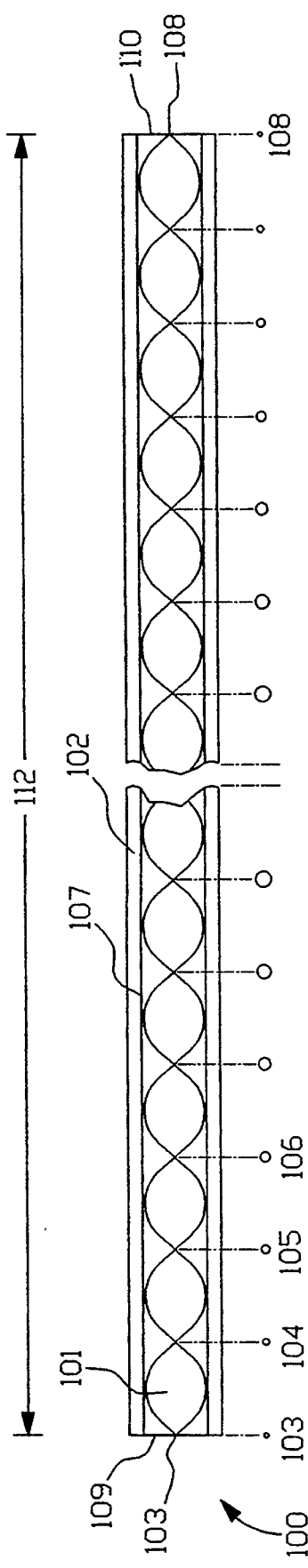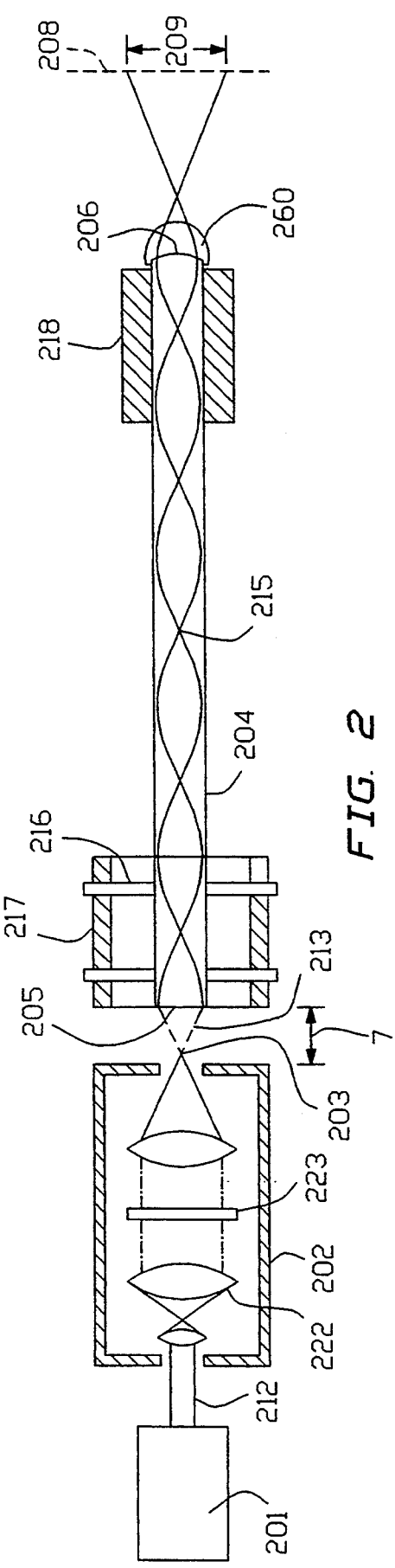

MULTIPLE EFFECT LASER DELIVERY DEVICE AND SYSTEM FOR MEDICAL PROCEDURES

REFERENCE TO RELATED CASE

This application is a continuation-in-part of copending U.S. patent application Ser. No. 07/908,379, filed on Jul. 6, 1992 by Wolfgang Neuberger, inventor, entitled "Multiple Effect Medical Laser Delivery System".

BACKGROUND OF THE INVENTION

1. Field of the Invention

The invention generally relates to a laser device and system method used to perform various surgical procedures, and more specifically to a medical laser delivery device and system employing at least one graded index optical fiber and means of altering laser beam's output characteristics.

2. Information Disclosure Statement

Medical laser delivery devices and systems are becoming increasingly more important for effectively performing procedures such as tissue cutting, coagulating, welding, and destroying kidney stones. Traditionally, these systems consist of a laser source, input optics, one or more flexible optical fibers, and an output end or handpiece. For example, U.S. Pat. No. 4,421,382 to Doi et al. and U.S. Pat. No. 5,102,410 to Dressel disclose laser delivery systems and their respective components. These laser systems and devices may also incorporate accessory devices such as cooling means, positioning means, vision fibers, or sensing fibers. The configuration of a particular laser delivery system depends upon the specific surgical application.

Perhaps the most important parameter to consider when configuring a laser delivery system is the interaction of the laser beam with the tissue. This interaction is largely a function of the laser's power density at the target. For example, cutting and coagulation require different power densities. Power density also controls the burn-off of residues from the output end of delivery system. Presently, the prior art employs step index fiber and special tips to control the output power density.

In a step index fiber, the laser beam becomes dispersed, losing its focal points as it propagates down the fiber. Because the laser beam lacks focal points, its density becomes redistributed across the whole diameter of the fiber's core. The power density thus becomes a function of the core's cross-sectional area. Consequently, to increase power density, the diameter of the fiber must be decreased. As the cross section area becomes smaller, however, it becomes more difficult to project the laser beam into the fiber. Thus, the prior art's control over power density becomes limited by the fiber's core size. Prior art devices face this limitation.

This limitation of prior art devices requires the attachment of sculptured sapphire tips to the end of the delivery device as described in U.S. Pat. No. 4,693,244 to Daikuzono. These tips focus the laser to a specific power density depending upon the specific surgical or medical application. Although effective in altering power density, changing tips during the operation can be difficult. For example, in the same operation, an operator may initially use the laser system to make an incision, and later use it to coagulate. This requires changing the sapphire tips at the end of the delivery fiber. Often, however, the output end may not be readily accessible, especially if it lies within the patient or if its sterility might be jeopardized. Therefore, the prior art is limited by its need to access the output end of the delivery system to alter power density. Therefore, a need arises to both control and monitor output power density at the input of the fiber.

Tanaka (U.S. Pat. No. 4,576,160) discloses a method to vary the spot size (and thus the power density) by a two step approach namely by changing the fiber used for transmission to one of the appropriate diameter as a coarse regulation and employing variable optics at the output end for fine regulations. It is thus clear that this prior art cannot overcome the inherent limitations in the transmission power density resulting from the use of the step index fiber and that it further suffers from the need to change the transmission fiber used altogether or to insert a number of fibers into the patient to be endoscopically treated, thus drastically increasing the channel diameter of the incision required. The variable optics on the output end are also difficult to practice in an endoscopic situation: its total space requirement may be prohibitively large and the control means (such as wires) to alter its characteristics during the coarse of a medical procedure without removing the device from the body would further add to the overall diameter of the device.

The laser beam's dispersion in a step index fiber not only limits the prior art's ability to control output power density, but also limits its ability to monitor the same for feedback purposes. To monitor output, the prior art requires monitoring the output power density at the output end of the delivery fiber. For example, the U.S. Pat. No. 4,693,244 and 5,050,597 both to Daikuzono require thermal sensing means, such as a thermocouple, located at the output end to provide feedback. Although U.S. Pat. No. 5,057,099 to Rink monitors infra-red radiation at the input end, Rink's invention is intended to monitor the temperature of the delivery device to insure that its maximum operating temperature is not exceeded. The Rink invention can only control the average over the cross section and over the whole fiber tip; it is unable to pinpoint local hot spots on the fiber end resulting, for instance, from small particles attached or burnt in. It does not monitor the output power density. Indeed, the prior art's use of a step index fiber prevents monitoring local power density from the input end of the fiber.

SUMMARY OF THE INVENTION

It is the object of this invention to provide a new and highly flexible medical laser delivery device and system with means to change the radiation pattern delivered without the need to change or modify the output end or output optics. Said output optics or output end is frequently embodied in the body and/or is sterile and its change or modification or the change of the whole delivery device during the procedure is undesirable. Changing the input pattern while using conventional step index fibers cannot achieve the required result of control of the output pattern in a reliable manner because of beam spreading over the length of the device. The light becomes diffused over the length of the conventional step index fiber. It is therefore another object of the present invention to specify the requirements for the transmission fiber employed in the device. The transmissive optical fiber employed is an optical fiber having an input end and an output end, the input end being equipped with connection means for affixing it to the output optics of a laser. The optical fiber is further characterized by a predetermined refractive index monotonically declining from its maximum level in the center axis of said fiber according to the equation $$n^2(r) = n_o^2 - \omega^2 r^2 - 2\beta r^4$$

whereby n(r) denotes the value of the radially symmetric refractive index at any given distance (r) from said center axis until the fiber core to clad boundary is reached at r=a from whereon the refractive index may remain constant and the optical fiber is further characterized by a length L according to the equation $$L = m \times 4\pi^2 \times \frac{n_o}{\lambda(3\beta/\omega^2 + \omega^2/n_o^2)} + l$$

where m is a positive integer and $\lambda$ is the wavelength of the laser to which said laser delivery device is intended to be affixed to and $n_o$ is the refractive index in the center axis of said fiber and where $\omega^2$ and $\beta$ are constants describing the refractive index profile of said fiber and where l is within the range of $$-p \times 2\pi/\omega \leq l \leq p \times 2\pi/\omega$$

where p is a positive integer.

Another object of the invention is to achieve effective feedback control for the laser delivery device to control such important parameters as power output and output pattern.

Still another object of the invention is to provide a method of manufacturing a medical laser delivery device as described in the present invention comprising the steps of choosing a length $L_0$ equal or slightly longer than a convenient distance required between a laser source contemplated to be used for a medical procedure to be carried out and the site on the body where the medical procedure should take place and choosing a radius "a" smaller than one required to give an optical fiber sufficient flexibility to pass through an eventually required endoscope or body channels needed to access the site where the medical procedure should take place and choosing a refractive index differential $[n_o^2 - n^2(a)]$ larger than the sinus of the half angle of the laser output beam from the laser device and choosing the parameters $\omega^2$ and $2\beta$ so as to result in a length $L_1$ being approximately equal to $L_0$ and manufacturing an optical fiber exhibiting a refractive index with said parameters and cutting said fibers at a length $L_2$ somewhat longer than $L_0$ and focusing a laser beam from the medical laser source on the input end of said optical fiber and observing that output spot size and polishing the output end back by less than $2\pi/\omega$ until a minimal spot size on the output end is observed and then tuning the input wavelength $\lambda$ so as to further minimize the output spot size and then reducing the length of said optical fiber by a multiple of $2\pi/\omega$ so as to achieve closest to the distance $L_3$ derived from the equation with new compiled parameters $\omega^2$ and $2\beta$.

BRIEF DESCRIPTION OF THE DRAWINGS

The present invention, its advantages and objects will be more fully understood when the specification herein is taken in conjunction with the drawings appended hereto, wherein:

FIG. 1 shows a general schematic illustration of the refocusing and image reconstruction behavior in a medical laser delivery device fiber according to the present invention.

FIG. 2 shows a general schematic of the device and depicts the major components.

Figure 3:
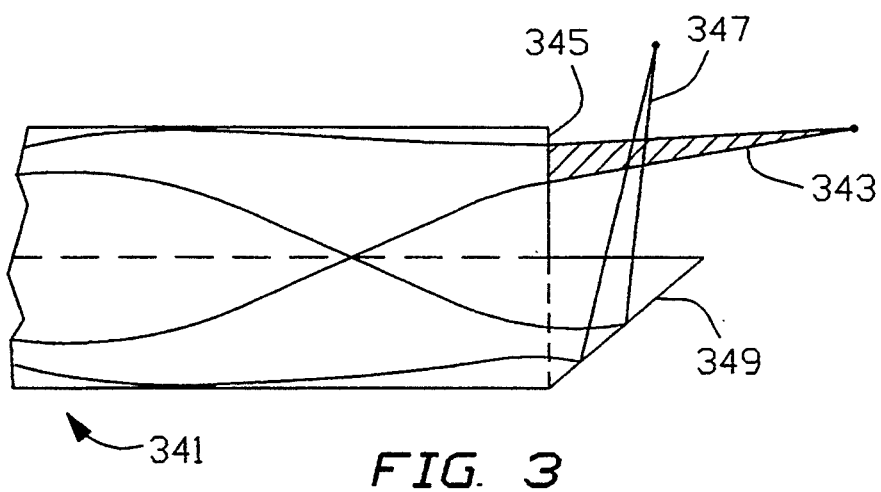
FIG. 3 illustrates the shaped output end of one preferred embodiment of the present invention.

DETAILED DESCRIPTION OF THE INVENTION.

In its simplest form, the medical laser delivery system and method of the present invention comprises the following optically connected elements: a coherent light source (a laser), an optical image formation and focusing system, a laser delivery device comprising at least one image transmitting graded index optical delivery fiber having an input end and an output end or handpiece (output optics). The image formation and focusing system may contain such components as lenses, windows, mirrors, prisms, electro-optic modulators and may contain means to alter the optical transmissions characteristics such as a step motor to move the components in an axial direction. The input end of the fiber is equipped with connection means for affixing it to the image formation and focusing system. The optical delivery fiber is further characterized by a predetermined refractive index profile. A laser beam is focused through the image formation and focusing system which, in its simplest form may be comprised of a single lens, into a focal plane and then coupled into the image transmitting graded index fiber. The relative position of the fiber input end face to the focal plane determines the spot size and divergence of the input beam entering the fiber. The spot size and divergence of the output beam further depend on the fiber length. Thus, by choosing the appropriate fiber length and relative positions between the fiber end face and focal plane of the lens, a wide range of output characteristics can be obtained.

The graded index fiber employed in the present invention laser delivery device exhibits a near parabola shaped refractive index profile, having the highest refractive index at the center and the lowest at the cladding boundary. The profile is mathematically calculated to periodically change the width of a laser beam as it propagates down the graded index optical delivery fiber. Consequently, the propagating laser beam converges at a multitude of refocus points along delivery fiber. This constant refocusing preserves the maximum power density. That is, the maximum power density is realized each time the beam converges at the refocus points.

The medical laser delivery device containing an optical fiber with a graded index profile resulting in periodic refocussing as described in the foregoing has some limitations, however, as shall be explained:

The refractive index variation in this refocusing graded index fiber can be described as $$n^2(r) = n_o^2/\cos h^2(\omega \times r) \quad \text{[Equation 1]}$$

for the core region of the fiber, meaning that the refractive index decreases as a function of the radius r from its maximum value $n^o$ in a radially symmetric form. For such a fiber, the refocusing distance is known to be $$d = 2\pi/\omega \quad \text{[Equation 2]}$$

and thus a function of the parameter $\omega$ characterizes the profile. Therefore, by choosing a transmission fiber with a multiple of this refocusing distance as its length $$l = m \times 2\pi/\omega \quad \text{[Equation 3]}$$

one should theoretically achieve the goal of being able to control the output power density from the input end as described.

In practical situations, however, it can be experimentally verified that the focus quality degrades over the length of the fiber from one refocusing point to the next. This is most noticeable when the length of the delivery fiber reaches several meters as is typical of most medical laser delivery devices (typically 1 to 4 meters). The reason for this gradual degradation lies in the imperfection of the profile and its practical departure from the ideal profile described by the above equation [1]. Therefore we found that, although the graded index profile and the periodic refocusing effect described above are useful to provide medical laser delivery devices and systems that can far exceed the power densities reached by the presently employed step index fibers, and while such new devices allow the control of the output power density to an extent very interesting for some applications, they still have shortcomings when larger delivery length (1-4 meters) and high power densities are required.

By using a fiber with a refractive index change over its core described by $n^2(r) = n_o^2 - \omega^2 r^2 - 2\beta r^4$ [Equation 4]

with the parameter $\beta$ being small compared to $\omega^2/2a^2$ and a being the core radius, it was discovered that the focus point is nevertheless reconstructed periodically over longer lengths and the corresponding periodicity length (z) is given by the equation:

$$z = 4\pi^2 \times \frac{n_o}{\lambda(3\beta/\omega^2 + \omega^2/n_o^2)} \quad \text{[Equation 5]}$$

This effect of long term focus (or image) reconstruction can be theoretically predicted by appropriate perturbation theory calculations. To practically carry out this invention, it is necessary to manufacture optical fibers with the profile indicated in the equation $$n^2(r) = n_o^2 - \omega^2 r^2 - 2\beta r^4 \quad \text{[Equation 4]}$$

with great accuracy. This can practically be achieved by the PCVD (plasma assisted chemical vapor deposition) method whereby very thin layers with varying dopand contents are successively deposited inside a quartz glass tube. This method provides the possibility to deposit several thousand layers successively (as compared to the one hundred to two hundred layers in the classical CVD or OVD processes.) After collapsing the preform thus obtained with the help of a high temperature flame on a lathe it is drawn into fiber of the desired diameter( for instance 600 $\mu$m cone diameters, 840 $\mu$m cladding diameters) and coated with a protective polymer layer (such as epoxy acrylate) on a draw tower. By using the results of refractive index profile measurements obtained by analyzing the preform before drawing with the help of a preform analyzer (example York Technologies P104) the effective parameters $n_o$, $\omega$ and $\beta$ can be determined and, knowing the desired operating wavelength $\lambda$ of the laser source, the periodicity z can be calculated. A preform analyzer determines the refractive index profile n(R), where R is the radial variable in the preform rod with a core radius A. From this, the refractive index in a fiber with core radius a can be readily determined following any fiber optic text book. The parameters $\omega^2$ and $2\beta$ can now be determined mathematically as the coefficients of an appropriate Taylor series polynomial expansion of the profile in the vicinity of its maximum value of the refractive index $(n_o)$ at $r-0$ (that is at the center of its axis). To find the optimum length in spite of the manufacturing and measurement inaccuracies always present, the fiber should be cut longer than the theoretically derived optimum length $$L = m \times z \quad \text{[Equation 6]}$$

where m is the integer to arrive closest to L, the desired laser delivery device length for the medical procedure envisaged. Typical preferred values of m are 1, 2, 3 or 4.

By projecting a test image (such as a small focal point or a line) on the well polished input end of the fiber by means of an image formation and focusing system while employing a laser source whose wavelength is tunable in a region around the desired operating wavelength $\lambda$ and using a magnification optics to magnify the image received at the polished output end of the fiber, we now proceed as follows:

We polish the fiber back by less than $2\pi/\omega$ until we see a clear image at the output plane. This means we have reached a fiber length being a multiple of the normal periodicity $2\pi/\omega$. We also know that we are close to the optimum length because we have used the formula of equation [5] and cut close to this suggested length. By tuning the wavelength $\lambda$ we now try to further improve the image quality. Typically, we shall find that the image is improved at a wavelength somewhat smaller than the designed for wavelength. We can now adjust our earlier inaccurate measurement values of $\beta$ and $\omega^2$ using the formula of equation [5]. Inserting these new values into equation [5] we will now cut the fiber back by a multiple of $2\pi/\omega$ to arrive at a length L.

$$L = m \times 4\pi^2 \times \frac{n_o}{\lambda(3\beta/\omega^2 + \omega^2/n_o^2)} + l \quad \text{[Equation 7]}$$

with $$-2\pi/\omega \leq l \leq 2\pi/\omega \quad \text{[Equation 8]}$$

This effectively means we reach the optimum length for the long distance refocussing effect that occurs at integer multiples of the long distance periodicity z as closely as possible, that is within one period of the short distance refocusing effect period $2\pi/\omega$. It should be noted here that the long distance periodicity does not need to be an integer multiple of the short distance periodicity. However, this does not matter for practical purposes where the parameters $\beta$ and $\omega^2$ will be chosen so as to give values of z that are 100 to 1000 times bigger than $2\pi/\omega$. In practical applications we have found that the long term refocusing effect works well when the parameters are chosen so that m is smaller than 5 where the fiber is cut close to the optimum long distance periodic refocussing length to within 10 times the short distance refocusing length $2\pi/\omega$. It may well be that these practical limits may be extended over time as yet more perfect profile manufacturing becomes feasible. The fiber core radius a is typically chosen between 50 $\mu$m and 500 $\mu$m so as to allow enough power to be transmitted through the fiber and to obtain a fiber flexible enough for practical (primarily endoscopical) applications. The fiber length is practically between one and four meters to allow enough room between the laser source and the part of the body where the operation is performed and where the output beam is needed. The fibers are typically made out of doped quartz glass to cover a wavelength range from 180 nm to 2700 nm. Suitable dopands are fluorine and germanium in particular.

Aside from the optical fiber of a refractive index profile and length as described in the preferred embodiments above, the medical laser delivery device and system may have a predetermined shaped output end which can be used to further control the direction of the laser beam propagating down the delivery fiber. The fiber output end may be shaped so that a ray hitting the upper side of the fiber output end will exit straight, whereas a ray hitting the lower side of the shaped output end will be totally reflected providing the inclination angle of this fiber end portion is chosen to satisfy the optical condition for a total reflection, for instance, in air. It is thus possible to effectively control the angular direction of the output beam by directing the laser radiation at the input end of the laser delivery device from one side of the input end to the other. This can be achieved by various optical means. One example would be a reflective disk with a smaller eccentrically sitting aperture, said disk being rotated within the image formation and focusing system.

Alternatively to shaping the fiber output end itself, a system of lenses or other optical elements can be affixed to the output end of the laser delivery device to further enhance its versatility. Typical state of the art devices for medical procedures may include optical handpieces, that is, pencil like assemblies containing one or more lenses to focus the beam exiting the delivery fiber in a divergent manner from the typically employed prior art step index fibers in order to focus the beam on the target at a predetermined distance. The same can be done using a variant of the laser delivery device in the present invention, however, a much tighter focus point is achieved due to the graded index fiber's superior ability to preserve beam characteristic properties.

In one preferred embodiment of the present invention device, a separation gap between the main delivery fiber and a similar fiber piece in the handpiece can be used to control the radiation output pattern from the handpiece. The separation gap can be easily adjusted by the surgeon, for instance, by twisting of an adjustment screw.

Another preferred embodiment of the present invention employs a graded index lens, whose distance to the optical delivery fiber input end (effective focal gap) is adjustable by means of a step motor. This lens is thus the last optical element in the image formation and focusing system in this preferred embodiment. By varying the relative position between moving elements, for instance, with help of a motorized drive mechanism, the desired output spot can be obtained. The simplest motor mechanism to vary fiber input end position could be realized, for example, with the help of a step motor which moves back and forth the fiber input end relative to the lens or vice versa along their common axis. For effective control and automatic adjustment of the system a feedback mechanism is based on a known correlation between parameters of the output beam and the parameters of the input beam for a given length of fiber. This correlation can be determined, for example, by special measurement of the output pattern in dependence on the distance between the input fiber end and the lens or by measurement of the pattern of that part of the beam reflected from the input end face in dependence on the same distance using, for example, a beam splitter in the case of CW beam field or a rotating mirror in the case of a pulsed beam radiation. Taking into account the measured correlation, it is possible to control the output pattern by proper choice of mentioned distance and to realize this choice through automatic adjustment following the established correlation. To understand how this embodiment functions, it should be noted that the image generated by the rays on the output end of the medical laser delivery device is partially reflected there. This is due to the refractive index difference between the optical fiber and the surrounding environment (for example, air). The reflected image now travels back up the fiber and forms an identical image at the fiber input end if its length has been suitably chosen (in accordance with the equations provided). Now, if the optical length of the fiber is effectively changed, for instance by bending or stretching, the reflected image will be distorted (such as the image exiting from the fiber itself will be distorted from the desired image). By varying the effective focal gap between the graded index lens and the optical fiber input end, the image can be reconstructed. This process can be automated with the help of a beam splitter and an image analyzing system. Thus, in this embodiment, a feedback mechanism utilizing the reflected image traveling back through the delivery fiber allows for the reconstruction of the desired output pattern when undesired distortions occur during the procedure. For rapid variation of the fiber excitation conditions without the mechanical positioning of the fiber and lens, it may be useful to employ an electro-optic modulator, i.e. the optical element (lenses, windows, etc.) with optical parameters (coefficient of refraction, for example) dependent on applied electric field. Thus is possible to vary the focal distance of the lens and the fiber excitation conditions by variation of the applied electrical field.

In some practical situations, it may be more convenient to control the output beam without changing the relative position between the lens and fiber end face. In this case, one can employ an image transmitting graded index fiber of an appropriate profile consisting of two or more sections with appropriate lengths and butt joined together in such a way to provide the desired output beam. By changing the gap between the fiber sections, offset and/or tilt between axes of these fiber sections, one can control the output beam position, its shape and divergence. The variation of the beam position may be useful also for its transformation into a variation of direction of the beam irradiation by employing a suitable shaped fiber end face or tips of a suitable form affixed to the fiber end if this is required for specific applications.

In another preferred embodiment, the image formation of the beam can also be performed with the help of a focuser which combines the functions of a phase hologram and a mirror. The user should make a choice of a substrate for fabrication of a computer generated hologram or focuser depending on the wavelength of radiation. The field distribution at the element performing the image formation function may first be calculated with the help of a computer. The user should reproduce the calculated picture at the surface of the substrate, for example, covered with some photoresist material. After developing of the photoresist this picture can be transformed into a refractive index variation or into relief at the substrate surface performing the required phase correction.

For some applications, it may be desirable to generate a Bessel beam of zero order and then transmit it to the output face of the fiber. The Bessel beam is a beam with plane wavefront whose transverse field distribution is described by the Bessel function. It has a sharp central maximum with high density of the beam power mainly responsible for tissue cutting and low density side rings weakly interacting with the tissue for coagulation.

Bessel beams can be particularly well transmitted with the fibers as described in this invention. A remarkable property of the Bessel beam is that it is a mode of homogeneous media and therefore it does not diffract (spread) as it propagates through the homogeneous medium. The Bessel beams can be represented (and generated) as a superposition of plane waves whose wave vectors k belong to a conical surface. Nothing is changed in such superposition as the beam propagates through the homogeneous medium. Therefore the Bessel beam is diffraction free. Even being restricted in its cross section by some aperture (output cross section of the fiber) the Bessel beam diffracts much slower than a Gaussian beam whose width is equal to the width of the central maximum of the Bessel beam. Therefore a fiber irradiated with such Bessel beams may be employed as a needle-like optical scalpel whose output beam is insensitive to the variation of the distance between the fiber end face and the surface of an operated tissue. For example, if a Gaussian beam with a diameter of $d_1 = 5$ $\mu$m and wavelength $= 1$ $\mu$m is irradiated by the fiber output face, then the length of diffraction of the beam responsible for the accuracy of the longitudinal positioning of the beam waist is of about $d_1^2/\lambda = 25$ $\mu$m The Bessel beam with the same diameter d of its central maximum being restricted by the fiber core cross section with the diameter $d_2 = 600$ $\mu$m spreads only after propagation over a distance $d_1 d_2/\lambda = 3$ mm.

To generate Bessel beams a ring-like aperture placed at the back focal plane of a lens is very inefficient from the viewpoint of utilization of the laser beam power. Therefore, to generate the Bessel beam, it is better to use a computer generated hologram performing a phase shift in the input plane beam which is linearly proportional to the distance from the beam axis or to use a simple optical axicon (conical lens) performing the same linear phase shift.

An input beam with plane wavefront transforms after propagation through such linear phase correctors into a superposition of plane waves whose wave vectors k belong to a conical surface, i.e. into a Bessel beam. The central spot size of the beam is determined by parameters of the phase correctors (for example, by a top angle of the axicon) and it may therefore be controlled if required.

If desired, various tips may be used to further enhance the flexibility of the present invention device. Although it is an object of the present invention to obviate the need for changing sculptured tips in order to change output pattern and intensity during surgical procedures, crystal tips have certain advantages over a bare fiber including their greater heat resistance and their ability to be replaced during an operation if fouled or contaminated. Further, when used in conjunction with the present invention various modified tip characteristics may result in a desired initial output pattern which can then be further modified by employing various altering means at the input end of the fiber. Sometimes the surgical application requires a decrease in power density and therefore an enlarged output pattern and other times the reverse is required. To this end tips of different shapes can be affixed to output end of delivery fiber to achieve a modified tip.

FIG. 1 shows a general schematic illustration of the refocusing and image reconstruction behavior in a medical laser delivery device fiber having a length 12 according to the present invention including the fiber core 101, fiber cladding 102 and ray 107 travelling in the fiber. Point 103 represents the focus point of the laser ray as it enters the fiber input end and points 104,105, and 106 represent gradually distorted refocus points. Point 108 represents the focus point at the fiber output end which matches point 103 at the input end due to the fact that the fiber 100 was manufactured in accordance with the present invention method described above.

FIG. 2 provides a general schematic of the device, and depicts the major components. The invention includes a laser source 201 (a coherent light source) adapted for surgical use. Such lasers include excimer and nitrogen lasers for the UV-region of spectra, pulse-periodic and continuous wave Nd:YAG lasers, Ho-lasers and Tm-lasers, gold-vapor and copper-vapor lasers, Kr-lasers and Dye-lasers, Ti-sapphire and laser diode lasers. Laser source 201 emanates a laser beam 212 with a distinct power, diameter, and divergence. Laser beam 212 leaves the laser source 201 and enters the optical image formation and focusing system 202. This system contains optical components such as lenses, as typified by lens component 222, windows, mirrors, prisms, electro-optic modulators, etc. as means to form the optical transmission characteristics. A window or aperture (not shown) in reflective disk component 223 within the optical image formation and focusing system 202 could be of various shapes depending on the procedure to be performed and the beam exiting through the aperture would take on a desired shape before entering delivery optical fiber 204. In its simplest form, the optical image formation and focusing system may be one condensing lens only focusing the (reasonably parallel) laser beam 212 from laser source 201 on a focal spot 203 to enter the input end 205 of a delivery optical fiber 204 which also has an output end 206 and handpiece 218. Focal spot 203 has a diameter less than the core of delivery optical fiber 204, and a divergence less than the fiber's numerical aperture (NA). The NA corresponds to the maximum divergence of laser beam 212 which can propagate down delivery optical fiber 204.

To axially align delivery optical fiber 204 with the converging laser beam 212, delivery optical fiber 204 is held in place with fiber optic connection means 216.

Connection means 216 are the various standard cable connectors such as SMA or ST, or similar connectors for mechanical fixation of the fiber in the center of a hollow cylinder 217. Once connected, the hollow cylinder 217 can be axially aligned with converging laser beam 212, and be axially moved to vary the distance between the focal spot 203 and the input end 205.

Delivery optical fiber 204 comprises a graded index fiber, the characteristics of which are critical to the present invention device and which further distinguishes the device over prior art devices employing step index fibers. The shortcomings of step index fibers are discussed above. As explained above, a graded index fiber exhibits a refractive index profile, having the highest refractive index at the center and the lowest at the cladding boundary. The profile is mathematically calculated to periodically refocus laser beam 212 as it propagates down delivery fiber 204. Consequently, laser beam 212 converges at a multitude of refocus points 215 along delivery fiber 204. This constant refocusing preserves the maximum power density. That is, the maximum power density is realized each time the beam converges at refocus points 215. The location along delivery fiber 204 of refocus points 215 depends upon the refractive index profile, and the effective focal gap 207. Therefore, for a given fiber, altering the effective focal gap 207 will shift the location of refocus points 215 in the delivery fiber 204. Laser beam 212 leaves the delivery fiber 204 at an output end 206, strikes a target 208, and forms an output pattern 209. Output pattern 209 is an established term in optics, and essentially means the spatial distribution of a laser beam's power intensity over the laser beam's cross-sectional area. Thus, output pattern 209 is the visual manifestation of power density; the wider the output pattern the lower the power density, and vice versa. Such graded index fibers are known to exist, one example of which is represented by German Patent No. 0 438 653 A2. However, the full advantages of the present invention are realized only if graded index fibers with profiles given by equation [4] and a length L as shown in equation [7] are used. In this case, the image representation is nearly perfect even over the longer length devices of practical interest.

The size of output pattern 209 is a critical parameter when performing surgery. If the output pattern is decreased, the power density rises which may be required for particular applications such as cutting. Similarly, if the output pattern is increased, the power density decreases which may be desired for certain applications such as coagulating. Therefore, the output pattern needed depends upon the surgical application, and this application may change in the course of a single operation.

The size, shape and density of output pattern 209 depends upon various factors including the characteristics imparted to laser beam 212 by the image formation and focusing system 202, geometry of output end 206, the distance from output end 206 to target 208, the effective focal gap 207 and the length of the gradient index delivery fiber 204. Optionally, surgical tips as are known in the art, such as sapphire tip 260 could be affixed to output end 206 to further control the shape and density of output pattern 209.

In one preferred embodiment, by shaping the output end, for instance as shown in FIG. 3, further control of the direction of the laser beam propagating down the delivery fiber is achieved. As shown, fiber output end 341 may be shaped so that laser beam ray 343 hitting the upper side 345 of the fiber output end 341 will exit straight, whereas laser beam ray 347 hitting the lower side 349 of the shaped output end 341 will be totally reflected providing the inclination angle of this fiber end portion is chosen to satisfy the optical condition for a total reflection, for instance, in air. It is thus possible to effectively control the angular direction of the output beam by directing the laser radiation at the input end of the laser delivery device from one side of the input end to the other. This can be achieved by various optical means. One example would be a reflective disk with a smaller eccentrically sitting aperture, said disk being rotated within the image formation and focusing system.

Figure 4:
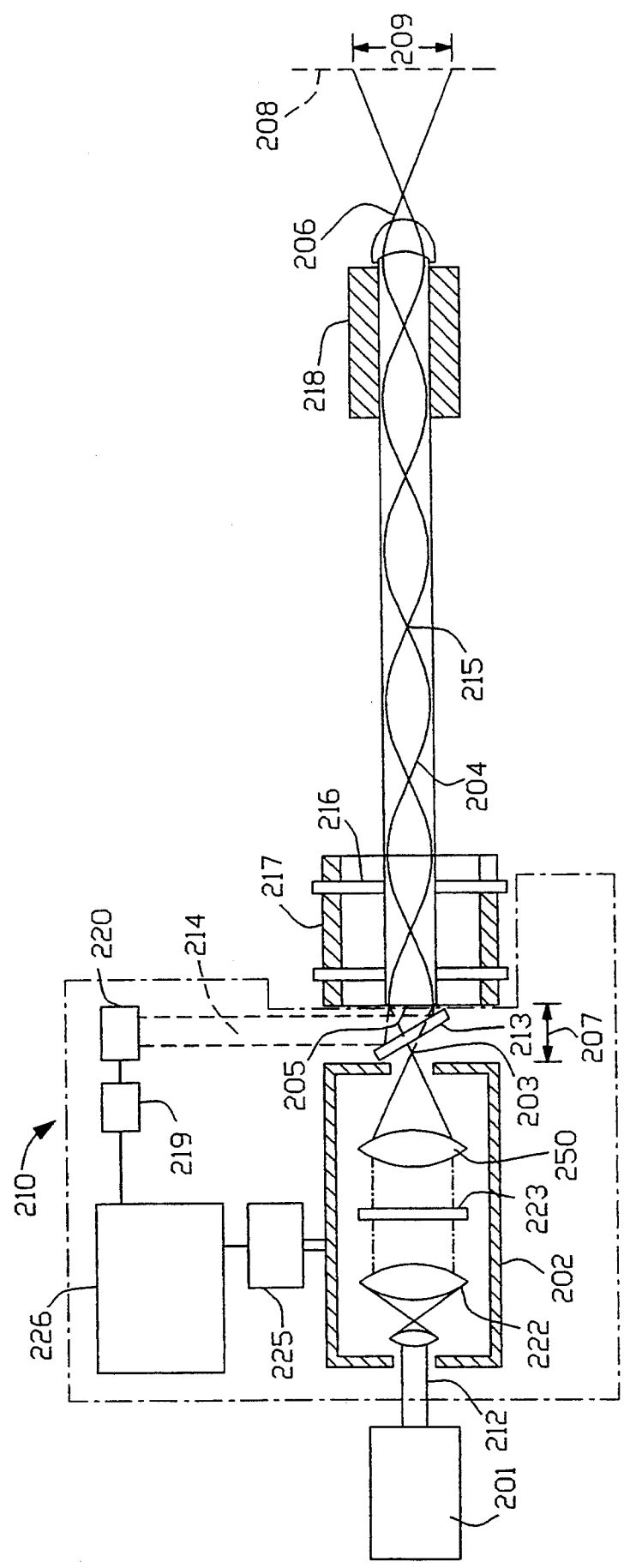
FIG. 4 shows a general schematic illustration of the device of the present invention including a feedback system.

FIG. 4 shows a preferred embodiment wherein like parts are like numbered to those in FIG. 2. A feedback system 210 comprised of those components within the dashed lines is employed in this embodiment. As shown, graded index lens 250 is the last component in the image formation and focusing system 202. Its distance to the input end 205 of delivery fiber 204 is adjustable by means of a step motor 225. Thus, output pattern 209 is controlled by altering effective focal gap 207. Such a step motor could be, for example an electric motor connected to an electric power source. In this embodiment, reflected laser light 214 from input end 205 of delivery fiber 204 is directed by partial mirror 213 onto feedback screen 220. The reflected image on feedback screen 220 is fed into image analyzing system 219 which has been pre-programmed to compare the reflected image with the desired image and which sends a signal to step motor control means 226 which controls step motor 225 so that the image formation and focusing system including graded index lens 250 can be moved axially in order to change effective focal gap 207. By use of such a feedback system, distortions in output pattern 209 can be corrected.

Figure 5:
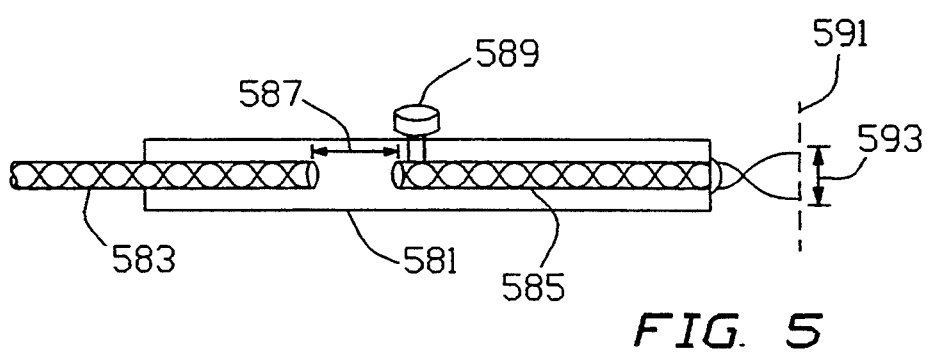
FIG. 5 shows an alternative output end including handpiece according to the present invention.

In FIG. 5 an alternative output end of the delivery device is shown. In such an embodiment the delivery fiber is split so that a separation gap 587 exists between the main delivery graded index fiber 583 and a similar graded index fiber piece 585 in handpiece 581. Separation gap 587 can be adjusted by means of, for instance, adjustment screw 589 located on the handpiece 581 thus affording the surgeon additional control of the output pattern 593 directed at target 591.

Figure 6:
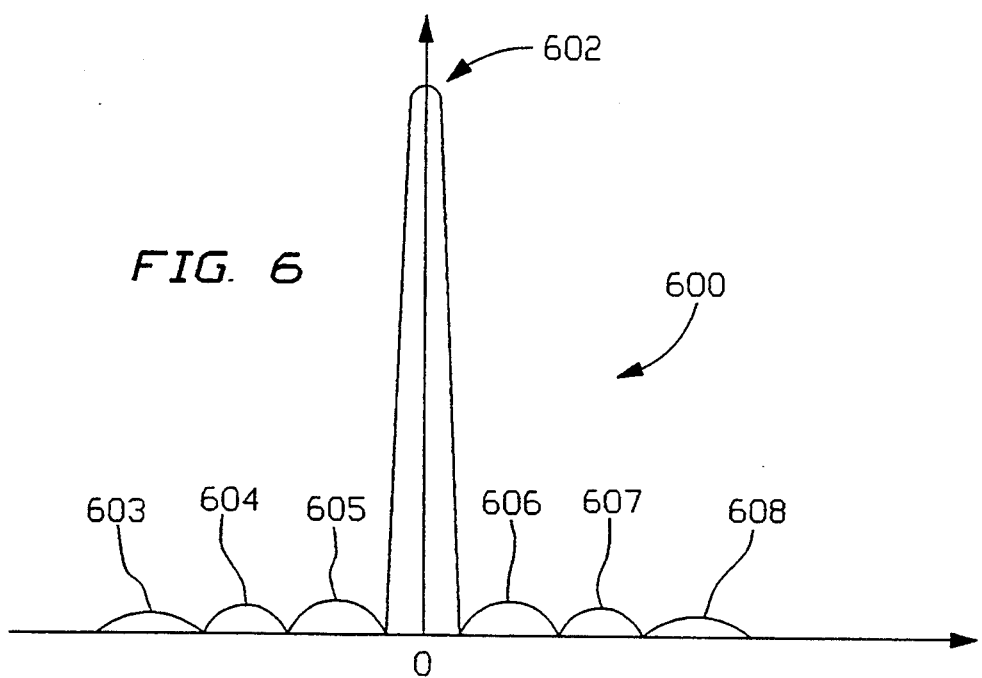
FIG. 6 shows a Bessel Beam intensity pattern.

FIG. 6 shows the intensity distribution of a Bessel Beam 600 over the radius illustrating the needle like characteristics described above. It has a sharp central maximum 602 with high density of the beam power mainly responsible for tissue cutting and low density side rings 603, 604, 605, 606, 607 and 608 weakly interacting with the tissue for coagulation.

Figure 7:
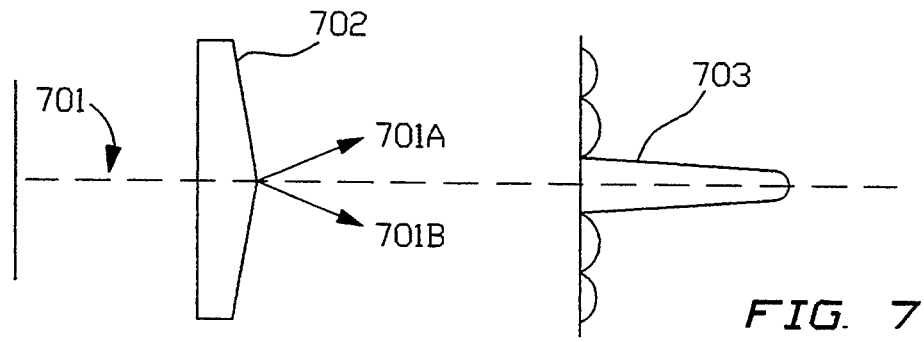
FIG. 7 shows a portion of an alternative embodiment of the present invention utilizing an axicon.

FIG. 7 shows vector 701 being transformed after passing through axicon 702 via transformed vectors $701_a$ and $701_b$ to give Bessel Beam shaped radiation 703.

Figure 8:
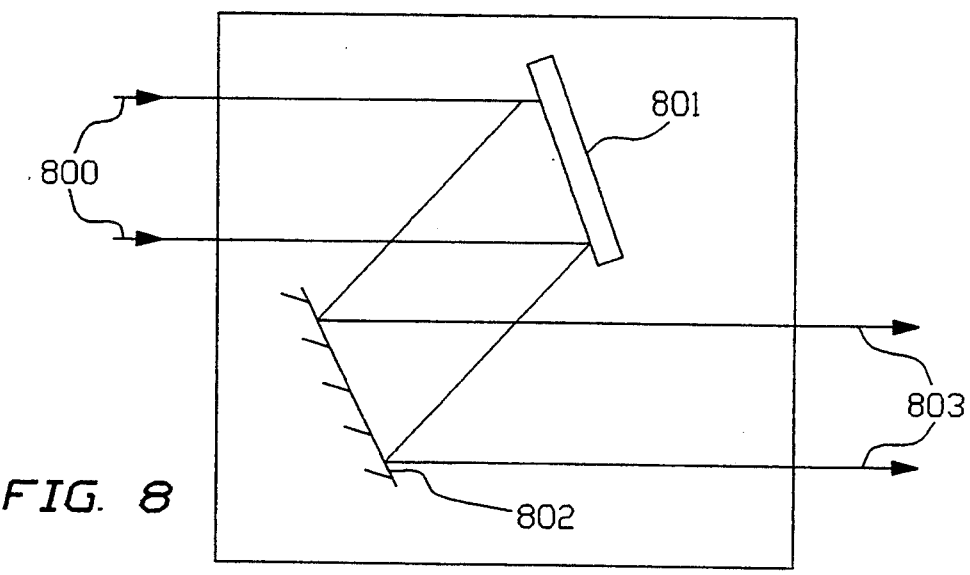
FIG. 8 shows a computer generated hologram being inserted into the laser path in an alternative preferred embodiment of the present invention.

FIG. 8 shows how a computer generated hologram can be inserted into the laser beam path wherein component 800 represents a parallelized laser beam coming from a laser source and component 801 is a computer generated hologram. The image is reflected from mirror 802 and exiting beam 803 is transmitted towards refocusing optics known in the art.

In light of the above described embodiments it must be understood that many variations of the invention can be created. The embodiments shown depict the best mode of the invention but it is obvious that numerous shapes sizes and orientations can be used for all the parts described. It should be therefore understood that in light of the appended claims, the invention may be practiced other than as specifically described, and individual features described in differing embodiments may be modified, combined or used in orientations other than those shown.

What is claimed is:

1. A medical laser delivery device comprising at least one optical fiber having an input end and an output end, said input end being equipped with connection means for affixing it to the output optics of a laser, said optical fiber being further characterized by a predetermined refractive index monotonically declining from its maximum level in the center axis of said fiber according to the equation $$n^2(r) = n_o^2 - \omega^2 r^2 - 2\beta r^4$$

whereby n(r) denotes the value of the radially symmetric refractive index at any given distance (r) from said center axis until the fiber core to clad boundary is reached at r=a from whereon the refractive index may remain constant and wherein said optical fiber is further characterized by a length L according to the equation $$L = m \times 4\pi^2 \times \frac{n_o}{\lambda(3\beta/\omega^2 + \omega^2/n_o^2)} + l$$

where m is a positive integer and $\lambda$ is the wavelength of the laser to which said laser delivery device is intended to be affixed to and $n_o$ is the refractive index in the center axis of said fiber and where $\omega^2$ and $\beta$ are constants describing the refractive index profile of said fiber and where l is within the range of $$-p \times 2\pi/\omega \leq l \leq p \times 2\pi/\omega$$

where p is a positive integer.

2. The medical laser delivery device of claim 1 further characterized by the positive integer m being smaller than 5 and the positive integer p being smaller than 10 and the parameter a (the radius of the fiber core) being chosen between 50 μm and 500 μm.

3. The medical laser deliver device of claim 2 further characterized by having a fiber core manufactured from doped quartz glass and further characterized by the parameter $\lambda$ (the wavelength of the laser) being between 180 nm and 2700 nm.

4. A medical laser delivery system comprising the following optically connected elements: a coherent light source (a laser), an optical image formation and focusing system, a laser delivery device comprising at least one optical fiber having an input end and an output end, said input end being equipped with connection means for affixing it to the output optics of a laser, said optical fiber being further characterized by a predetermined refractive index as claimed in claim 1 and a predetermined length as claimed in claim 1 and eventually, an output optics.

5. The laser delivery system of claim 4 wherein said optical image formation and focusing system further includes means to vary a focal spot size at said input end of said optical fiber.

6. The medical laser delivery system of claim 4 wherein said optical image formation and focusing system further includes adjustable means to alter an image formed in shape, size and power distribution.

7. The medical laser delivery system of claim 5 wherein said image formation and focusing system compensates distortions in the output image that may be caused by bending, stretching and other distortions of said laser delivery device, said compensation being achieved by displacing at least one optical component contained in said image formation and focusing system until an undistorted desired output image re-appears via reflection from said output end of said optical fiber at said optical component and matches the input image at said input end of said optical fiber.

8. The medical laser delivery system of claim 7 wherein said optical component is a graded index lens.

9. The medical laser delivery system of claim 6 wherein said image formation and focusing system compensates distortions in the output image that may be caused by bending, stretching and other distortions of said laser delivery device, said compensation being achieved by displacing at least one optical component contained in said image formation and focusing system until an undistorted desired output image re-appears via reflection from said output end of said optical fiber at said optical component and matches the input image at said input end of said optical fiber.

10. The medical laser delivery system of claim 9 wherein said optical component is a graded index lens.

11. The medical laser delivery system of claim 6 wherein said image formation and focusing system includes at least one beam splitter that directs an image received from the output end of said optical fiber to a laser beam profile analyzer thus enabling detection of hot spots or fiber damage onset.

12. The medical laser delivery system of claim 4 wherein said image formation and focusing system includes at least one axicon to form a Bessel Beam thus achieving a scalpel shaped beam at said output end of said optical fiber.

13. The laser delivery device of claim 7 wherein said output end is formed into a predetermined shape.

14. The laser delivery device of claim 7 wherein said output end is affixed with at least partially transmissive optical elements formed into a predetermined shape.

15. The medical laser delivery system of claim 4 wherein said optical fiber is split and contains at least one variable gap in a path of said optical fiber and said medical laser delivery system includes means to change said gap.

16. The medical laser delivery device of claim 13 wherein said predetermined shape is chosen so as to transform a radial movement of a propagating laser beam into an angular deflection of said beam.

17. The medical laser delivery device of claim 14 wherein said predetermined shape is chosen so as to transform a radial movement of a propagating laser beam into an angular deflection of said beam.

18. The medical laser delivery system of claim 4 wherein said image formation and focusing system includes at least one computer generated hologram to form a Bessel Beam thus achieving a scalpel shaped beam at said output end of said optical fiber.

19. A method of manufacturing a medical laser delivery device as claimed in claim 2 comprising the steps of choosing a length $L_0$ equal or slightly longer than a convenient distance required between a laser source contemplated to be used for a medical procedure to be carried out and the site on the body where the medical procedure should take place and choosing a radius a smaller than one required to give an optical fiber sufficient flexibility to pass through an eventually required endoscope or body channels needed to access the site where the medical procedure should take place and choosing a refractive index differential $[n_o^2 - n^2(a)]$ larger than the sinus of the half angle of the laser output beam from the laser device and choosing the parameters $\omega^2$ and $2\beta$ so as to result in a length $L_1$ being approximately equal to $L_0$ and manufacturing an optical fiber exhibiting a refractive index with said parameters and cutting said fibers at a length $L_2$ somewhat longer than $L_0$ and focusing a laser beam from the medical laser source on the input end of said optical fiber and observing than output spot size and polishing the output end back by less than $2\pi/\omega$ until a minimal spot size on the output end is observed and then tuning the input wavelength $\lambda$ so as to further minimize the output spot size and then reducing the length of said optical fiber by a multiple of $2\pi/\omega$ so as to achieve closest to the distance $L_3$ derived from the equation with new compiled parameters $\omega^2$ and $2\beta$.

* * * * *